(12) United States Patent
Charlton

(10) Patent No.: US 7,723,113 B2
(45) Date of Patent: May 25, 2010

(54) PACKAGING SYSTEM FOR TEST SENSORS

(75) Inventor: Steven C. Charlton, Osceola, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 572 days.

(21) Appl. No.: 10/207,102

(22) Filed: Jul. 30, 2002

(65) Prior Publication Data
US 2003/0036200 A1 Feb. 20, 2003

Related U.S. Application Data

(60) Provisional application No. 60/313,971, filed on Aug. 20, 2001.

(51) Int. Cl.
*G01N 33/49* (2006.01)
(52) U.S. Cl. .............................. 436/46; 436/43; 436/95; 422/63
(58) Field of Classification Search .................... 422/63; 436/43, 46, 95
See application file for complete search history.

(56) References Cited

U.S. PATENT DOCUMENTS

| | | | |
|---|---|---|---|
| 3,651,927 A | 3/1972 | Richardson et al. |
| 4,948,737 A | 8/1990 | Quenin et al. |
| 5,167,922 A | 12/1992 | Long |
| 5,194,393 A | 3/1993 | Hugl et al. |
| 5,332,549 A | 7/1994 | MacIndoe, Jr. |
| 5,429,735 A | 7/1995 | Johnson et al. |
| 5,575,403 A | 11/1996 | Charlton et al. |
| 5,609,823 A | 3/1997 | Harttig et al. |
| 5,620,579 A | 4/1997 | Genshaw et al. |
| 5,630,986 A | 5/1997 | Charlton et al. |
| 5,645,798 A | 7/1997 | Schreiber et al. |
| 5,653,863 A | 8/1997 | Genshaw et al. |
| 5,660,791 A | 8/1997 | Brenneman et al. |
| 5,679,311 A | 10/1997 | Harttig et al. |
| 5,720,924 A | 2/1998 | Eikmeier et al. |
| 5,723,284 A | 3/1998 | Ye |
| 5,738,244 A | 4/1998 | Charlton et al. |
| 5,757,666 A | 5/1998 | Schreiber et al. |
| 5,759,364 A | 6/1998 | Charlton et al. |
| 5,788,064 A | 8/1998 | Sacherer et al. |
| 5,798,031 A | 8/1998 | Charlton et al. |

(Continued)

FOREIGN PATENT DOCUMENTS

EP 01 118 856 A1 7/2001

(Continued)

*Primary Examiner*—Lyle A Alexander
(74) *Attorney, Agent, or Firm*—Nixon Peabody LLP

(57) ABSTRACT

A testing device for analyzing the glucose concentration of a sample of blood is adapted to remove a test sensor from a sensor package. The testing device comprises an inlet region and a puncturing member The inlet region receives a portion of the sensor package extending inward from an outer periphery of the test sensor package. The puncturing member is adapted to extend into the inlet region, puncture the sensor package, and to engage a mating feature of the test sensor. The puncturing member is adapted to hold the test sensor in the inlet region in a manner allowing the package to be removed and is adapted to hold the test sensor in the inlet region during testing a blood sample.

33 Claims, 5 Drawing Sheets

U.S. PATENT DOCUMENTS

| | | |
|---|---|---|
| 5,810,199 A | 9/1998 | Charlton et al. |
| 5,854,074 A | 12/1998 | Charlton et al. |
| 5,856,195 A | 1/1999 | Charlton et al. |
| 6,176,119 B1 | 1/2001 | Kintzig |
| 6,377,894 B1 | 4/2002 | Deweese et al. |
| 6,600,997 B2 | 7/2003 | Deweese et al. |
| 6,773,671 B1 | 8/2004 | Lewis et al. |

2002/0169411 A1 * 11/2002 Sherman et al. ............... 604/48

FOREIGN PATENT DOCUMENTS

| | | |
|---|---|---|
| JP | 2000-171427 | 6/2000 |
| JP | 2001 033417 A | 2/2001 |
| JP | 2001 033418 A | 2/2001 |

* cited by examiner

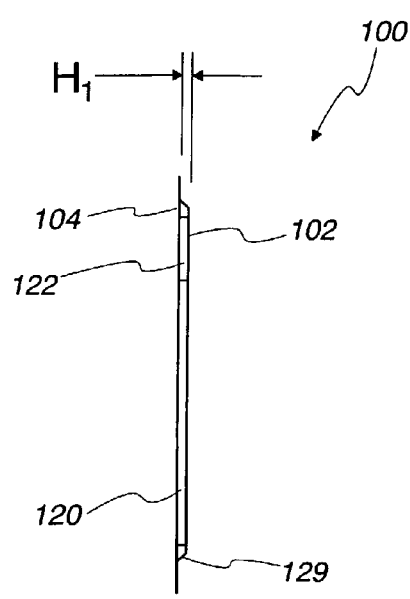
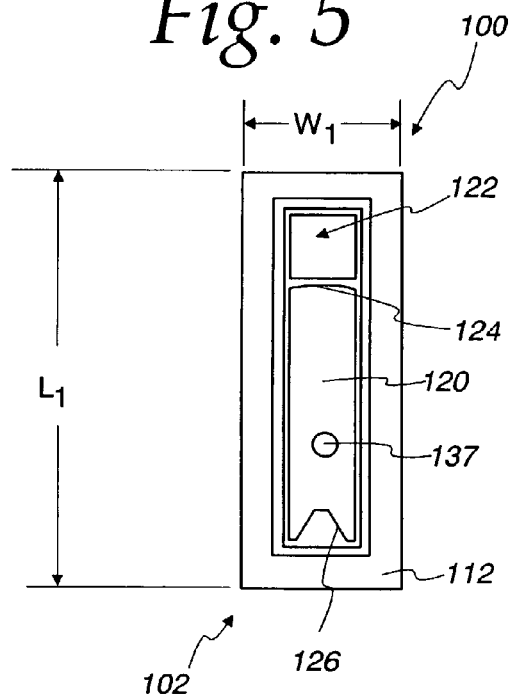
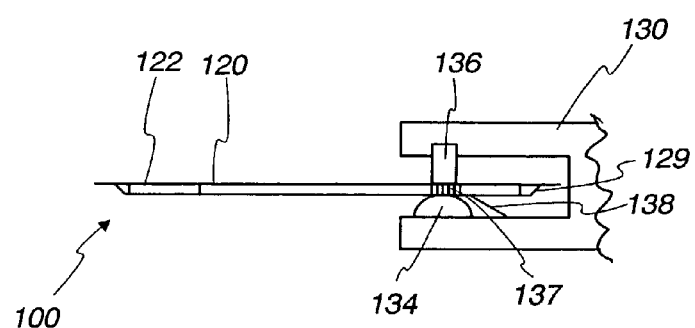
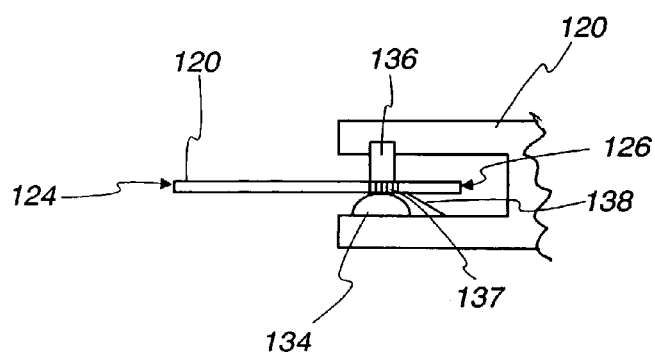

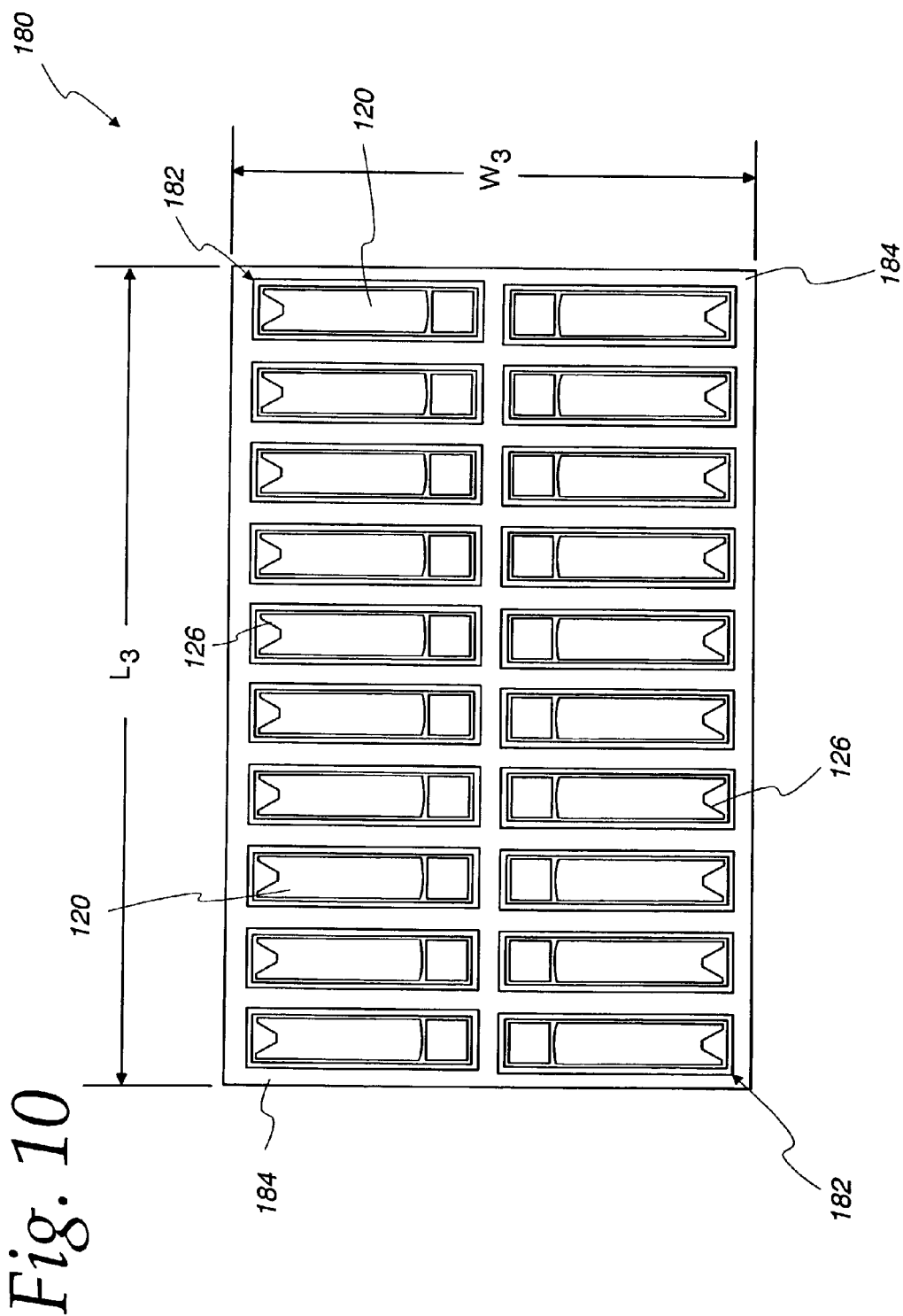

PACKAGING SYSTEM FOR TEST SENSORS

CROSS-REFERENCE TO RELATED APPLICATION

This application claims benefit to U.S. Provisional Application No. 60/313,971, filed on Aug. 20, 2001, which is incorporated by reference in its entirety.

FIELD OF THE INVENTION

The present invention relates generally to blood glucose monitoring systems for determining the concentration of glucose in blood, and more particularly, to a test sensor packaging system for use with blood glucose monitoring systems.

BACKGROUND OF THE INVENTION

It is often necessary to quickly obtain a sample of blood and perform an analysis of the blood sample. One example of a need for obtaining a sample of blood is in connection with a blood glucose monitoring system, which a user must frequently use to monitor the user's blood glucose level.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous, shaky, and confused. That person's judgment may become impaired and that person may eventually pass out. A person can also become very ill if their blood glucose level becomes too high—a condition known as hyperglycemia. Both conditions, hypoglycemia and hyperglycemia, are potentially life-threatening emergencies.

One method of monitoring a person's blood glucose level is with a portable, hand-held blood glucose testing device. The portable nature of these devices enables the users to conveniently test their blood glucose levels wherever the user may be. The glucose testing device includes a test sensor to harvest the blood for analysis. One type of test sensor is the electrochemical biosensors. The electrochemical biosensor includes a regent designed to react with glucose in the blood to create an oxidation current at electrodes disposed within the electrochemical biosensor which is directly promotional to the users blood glucose concentration. Such a test sensor is described in U.S. Pat. Nos. 5,120,420; 5,660,791; 5,759,364; and 5,798,031, each of which is incorporated herein in its entirety. Another type of sensor is an optical biosensor, which incorporates a reagent designed to produce a colorimetric reaction indicative of a users blood glucose concentration level. The colorimetric reaction is then read by a spectrometer incorporated into the testing device. Such an optical biosensor is described in U.S. Pat. No. 5,194,393, which is incorporated herein by reference in its entirety.

In order to check the blood glucose level, a drop of blood is obtained from the fingertip using a lancing device, and the blood is harvested using the test sensor. The test sensor, which is inserted into a testing unit, is brought into contact with the blood drop. The test sensor draws the blood, via capillary action, to the inside of the test unit which then determines the concentration of glucose in the blood. Once the results of the test are displayed on a display of the test unit, the test sensor is discarded. Each new test requires a new test sensor.

Referring now to FIGS. 1 and 2, an example of a testing device 10 and a package 30 of test sensors 12 ("sensor pack") are shown, respectively. The sensor pack 30 is designed to be housed within the testing device 10. Prior to each test, a collection end 14 of an individual test sensor 12 is pushed by a mechanism within the testing device 10 through its packaging and is extended from the test device 10 through a slot 16 for harvesting a sample of blood. The testing device includes a slider 18 for advancing the test tensor 12. In FIG. 1, a test sensor 12 is shown extending from the testing device 10. The collection end 14 extends from the testing device 10, while a contact end, that is the opposite end of the test sensor 12, remains inside the testing device 10. The contact end includes terminals that electrically couple the electrodes to a meter disposed within the testing device 10 for measuring the oxidation current produced at the electrodes by the reaction of glucose and the reagent. The test unit includes a display 20.

Referring now to FIG. 2, test sensors 12 are shown disposed in the sensor pack 30. The sensor pack 30 is made up of a circular disk 32 having ten individual compartments (blisters) 34 arranged radially. The disk is made from an aluminum foil/plastic laminate which is sealed to isolate the sensor from ambient humidity and from other sensors with a burst foil cover 36. Each test sensor 12 kept dry by a desiccant located inside a desiccant compartment 37 disposed adjacent the blisters 34. To retrieve a sensor, a mechanism disposed within the testing device 10, such as a knife, is driven down through the burst foil into an individual elongated compartment 34 at the end closest to the hub of the disk 32 and then moved radially toward the perimeter of the blister 34 In doing so, the knife engages the contact end 38 (fish tail) of the sensor in that compartment Radial travel of the knife pushes the tip of the sensor out through the burst foil and through parts of the testing device 10 such that the collection end of the sensor 12 is completely out of the testing device 10 and ready to receive a fluid test sample such as blood. For this stage, it is essential that the bond between the base and lid of the sensor withstand the sheer forces generated when the sensor bursts out through the foil. This method of providing a sensor ready for use is more fully described in U.S. Pat. No. 5,575,403, which is incorporated herein by reference in its entirety.

Further details of the operational and mechanical aspects of the testing device 10 and sensor pack 30 are more fully described in U.S. Pat. Nos. 5,575,403; 5,630,986; 5,738,244; 5,810,199; 5,854,074; and 5,856,195, each of which are hereby incorporated by reference in their entireties.

A drawback associated with testing devices which house a package of sensors is that the size of the package (i.e., the number of sensors in the package) is constrained by the device itself, thus making it difficult to modify the number of sensors per package. Accordingly, there exists a need for a testing system wherein the test sensor package size is independent of the testing device.

A drawback associated with the test sensor 12 of the device illustrated in FIGS. 1 and 2 is the somewhat pointed collection end (FIG. 2) of the 14 of the test sensor 12. The pointed end can be inconvenient and uncomfortable in collecting blood. The collection end 12 is pointed to puncture the foil cover 36 as the test sensor 12 is pushed from its individual compartment 34. A test sensor which has a substantially flat, nonpointed, collection end would more conveniently and comfortably collect a sample of blood.

SUMMARY OF THE INVENTION

A testing device for analyzing the glucose concentration of a sample of blood is adapted to remove a test sensor from a sensor package. The testing device comprises an inlet region and a puncturing member. The inlet region receives a portion of the sensor package extending inward from an outer periphery of the test sensor package. The puncturing member is adapted to extend into the inlet region, puncture the sensor package, and to engage a mating feature of the test sensor. The puncturing member is adapted to hold the test sensor in the inlet region in a manner allowing the package to be removed and is adapted to hold the test sensor in the inlet region during testing a blood sample.

The above summary of the present invention is not intended to represent each embodiment, or every aspect, of the present invention. Additional features and benefits of the present invention will become apparent from the detailed description, figures, and claims set forth below.

BRIEF DESCRIPTION OF THE FIGURES

Other objects and advantages of the invention will become apparent upon reading the following detailed description in conjunction with the drawings in which:

FIG. 4 is a side view of a test sensor pack for a single test sensor according to the present invention;

FIG. 5 is a top view of a test sensor pack for a single test sensor according to the present invention;

FIG. 6 is a side view of a test sensor pack inserted into a testing device according to the present invention;

FIG. 7 is a side view of a test sensor inserted into a testing device according to the present invention;

FIG. 10 is a test sensor pack card according to the present invention.

DETAILED DESCRIPTION OF THE ILLUSTRATED EMBODIMENTS

Figure 3:
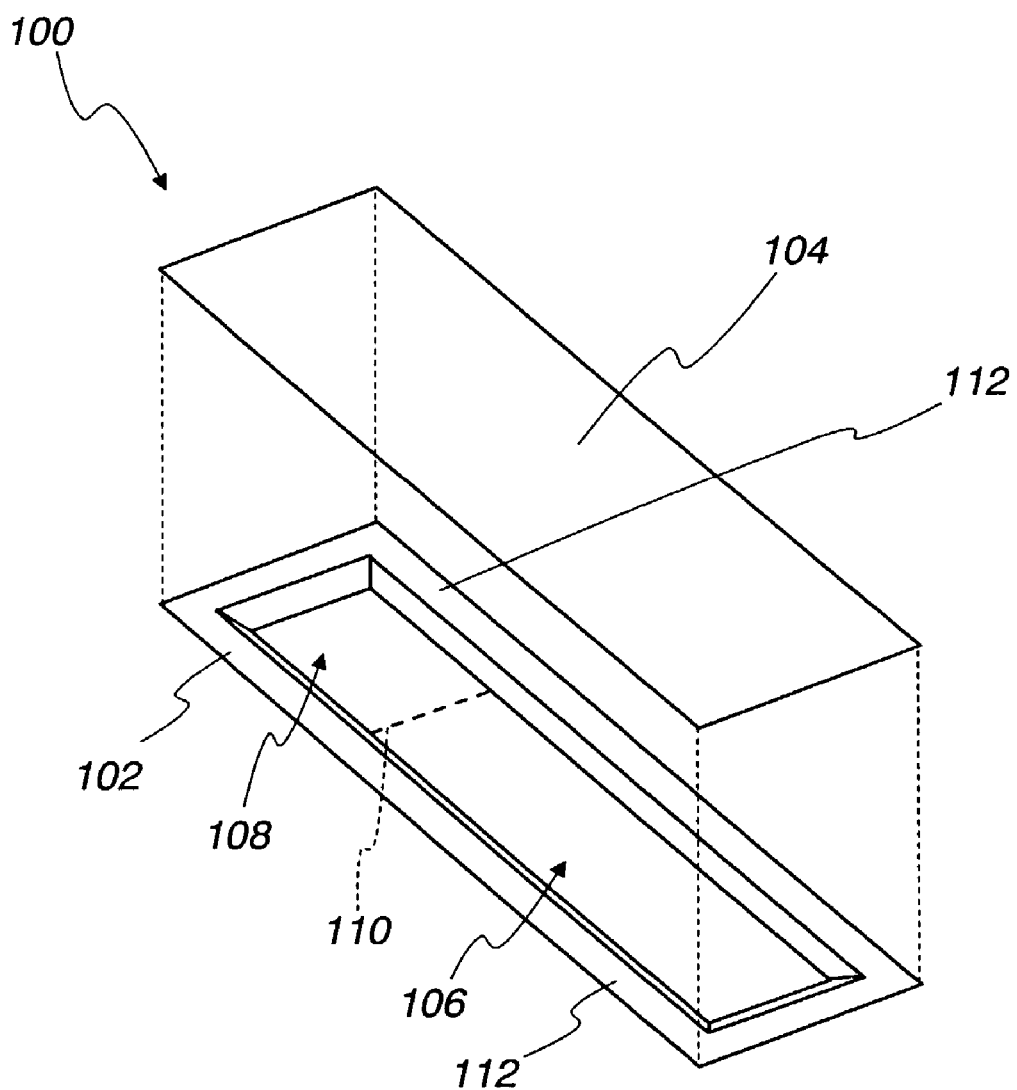
FIG. 3 is a perspective view of a lid and a base plate of a single test sensor according to the present invention

Referring now to FIGS. 3, 4, and 5, a single sensor pack 100 for a single test sensor is shown The sensor pack 100 includes a base 102 and a foil cover 104. The base 102 includes a test sensor cavity 106 one end of which comprises a desiccant cavity 108. In the illustrated embodiment, the test sensor cavity 106 is shown separated by the desiccant cavity by a dashed line 110. In an alternative embodiment of the present invention, the dashed line may represent a raised portion such as a wall that maintains a desiccant 122 (FIG. 5) and a test sensor 120 (FIG. 5) in their respective cavities. Such a wall should be sized to still allow vapor communication between the desiccant cavity 108 and the test sensor cavity 106 so that the desiccant may properly maintain the humidity of the test sensor cavity 106 as is described in greater detail below.

The foil cover 104 is adapted to cover the base 102 and to be affixed to the base 102 by sealing along the entire outer peripheral edge of the foil cover 104 to an outer peripheral edge 112 of the base 102. The foil cover 104 may be made of any material that will adequately seal the test sensor and desiccant cavities 106, 108 while providing a material than can be easily severed when extracting a test sensor 120 from the sensor cavity 106 as is described below. According to one embodiment of the present invention, the foil cover 104 is made out of AL-191-01 foil distributed by alGroup Wheaton.

The test sensor pack 100 is constructed so that the test sensor cavity 106 is in vapor communication with the desiccant cavity 108. The desiccant cavity 108 is formed of a small depression in the base 102 adjacent the test sensor cavities 106. A desiccant material is disposed in the desiccant cavity 108 in order to maintain the test sensor cavity 106 at an appropriate humidity level so that the reagent material disposed within the test sensor 120 is not adversely affected prior to being used. The desiccant material 122 is in the form of a small bag or round bead of material or any other form that can be readily disposed in the desiccant cavity 108. The amount of such desiccant material placed in the desiccant cavity 108 will be dependent on the amount that is required to maintain the sensor cavity 106 in a desiccate state. One type of desiccant material that can be used is 13X synthetic molecular sieves from Multisorb Technologies Inc. of Buffalo, N.Y., available in powder, pellet, and bead forms.

Referring now to FIGS. 4 and 5, a side view of a sensor pack 100 and a top view of the sensor pack 100 (with the foil cover 104 removed) are shown, respectively, having a test sensor 120 disposed within the sensor cavity 106 and a desiccant 122 disposed within the desiccant cavity 108. The test sensor 120 is disposed within the sensor pack such that a collection end 124 of the test sensor 120 is disposed adjacent the desiccant cavity 108. A contact end 126 of the test sensor 120 is disposed towards the end of the test sensor pack 100 opposite the desiccant cavity 108. The test sensor collection end 124 includes a capillary inlet (not shown) for collecting a sample of blood. The test sensor contact end 126 includes terminals (not shown) for electrically coupling electrodes within the test sensor 120 to a testing device. The base 102 has an angled side wall 129, which facilitates the removal of the test sensor 120 from the sensor pack 100 as described below.

According to the embodiment of the sensor pack illustrated in FIGS. 4 and 5, the sensor pack 100 has a width $W_1$ of approximately 0.445 inches (about 11.30 mm), a length $L_1$ of approximately 1.170 inches (about 29.7 mm), and a height $H_1$ of approximately 0.038 inch (about 0.97 mm).

Referring to FIGS. 6 and 7, the removal of the test sensor 120 from the sensor pack 100 will be described. In operation, a testing device 130 is adapted to remove the test sensor 120 from the sensor pack 100. To load a test sensor 120, the sensor pack 100 is orientated with the contact end 126 of the sensor facing towards the testing device 130, and then the sensor pack 100 is pushed into the testing device 130 as shown in FIG. 6. A guide member 134 aides in the proper alignment of the sensor pack 100 within the testing device 130. Once the sensor pack 100 is pushed into the meter, a puncturing member such as a pin 136 is lowered by the testing device 130 such that it punctures the foil cover 104 and engages a mating component 137 of the test sensor 120. In the embodiment of the test sensor 120 illustrated in FIG. 5, the mating feature is an indentation 137 disposed in the test sensor 120. The pin 136 engages the test sensor 120 and presses the test sensor 120 against the guide member 134. The sensor pack 100 is then pulled away from the testing device 130 by the user, the pin 136 holds the sensor stationary against the guide member 134 causing the sensor 120 to burst out of the inward (toward the testing device 130) end of the sensor pack 100. As the sensor pack 100 is pulled away, the sloped side wall 129 of the base 102 drives the contact end 126 of the test sensor 120 against the foil cover. The contact end 126 of the test sensor 120, illustrated in FIG. 5, is pointed so that the test sensor 120 can more easily puncture the foil cover 104 and "burst" out of the sensor pack 100. The test sensor 120 is now in a testing position (FIG. 7) and is ready to be used to collect and analyze a sample of blood.

The testing device is designed so that once the package is removed, the test sensor 120 is properly aligned in the testing device 130 to conduct the test. The testing device includes terminals 138 that electrically couple the testing device 130 to the terminals (not shown) disposed on the test sensor 120. Once the test sensor 120 is in the testing position, the collection end 126 of the test sensor 120 is placed into a sample of blood, such as a sample of blood that is accumulated on a person's finger after the finger has been pricked. The blood is absorbed into the test sensor 120 and chemically reacts with the reagent material in the test sensor 120 so that an electrical signal indicative of the blood glucose level in the blood sample being testing is supplied to the terminals 138 and thereby to a meter disposed within the testing device 130 for measuring the electrical signal. The result of the analysis, that is the blood glucose level of the sample tested, is communicated to the user via a display (not shown) disposed on, or coupled to, the testing device 130.

The testing device 130 and sensor pack 100 illustrated in FIGS. 6 and 7 is advantageous over many prior art test sensors because the sample collection end 124 of the test sensor 120 never contacts or passes through the testing device 130. This arrangement removes the potential risk of cross-contamination in situations where the testing device 130 may be used by more than one patient.

Figure 1:
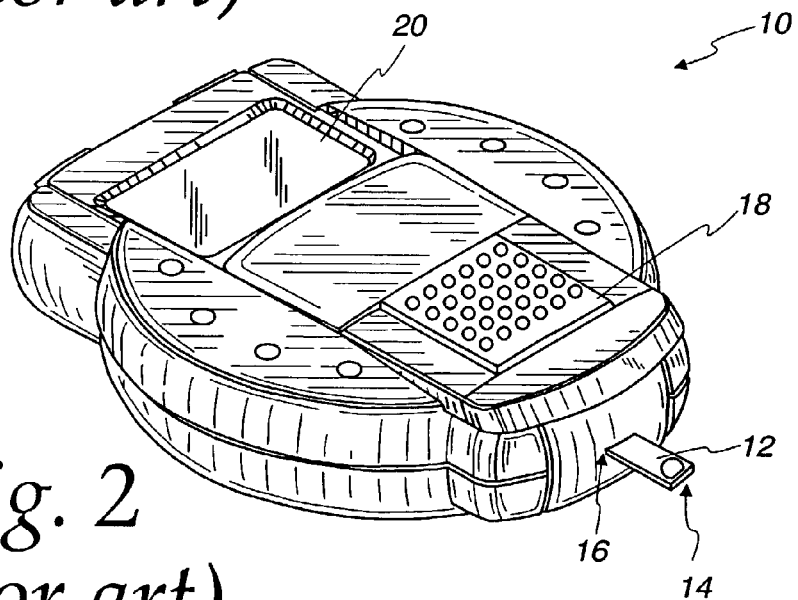
FIG. 1 is a perspective view of a prior art testing device.
Figure 2:
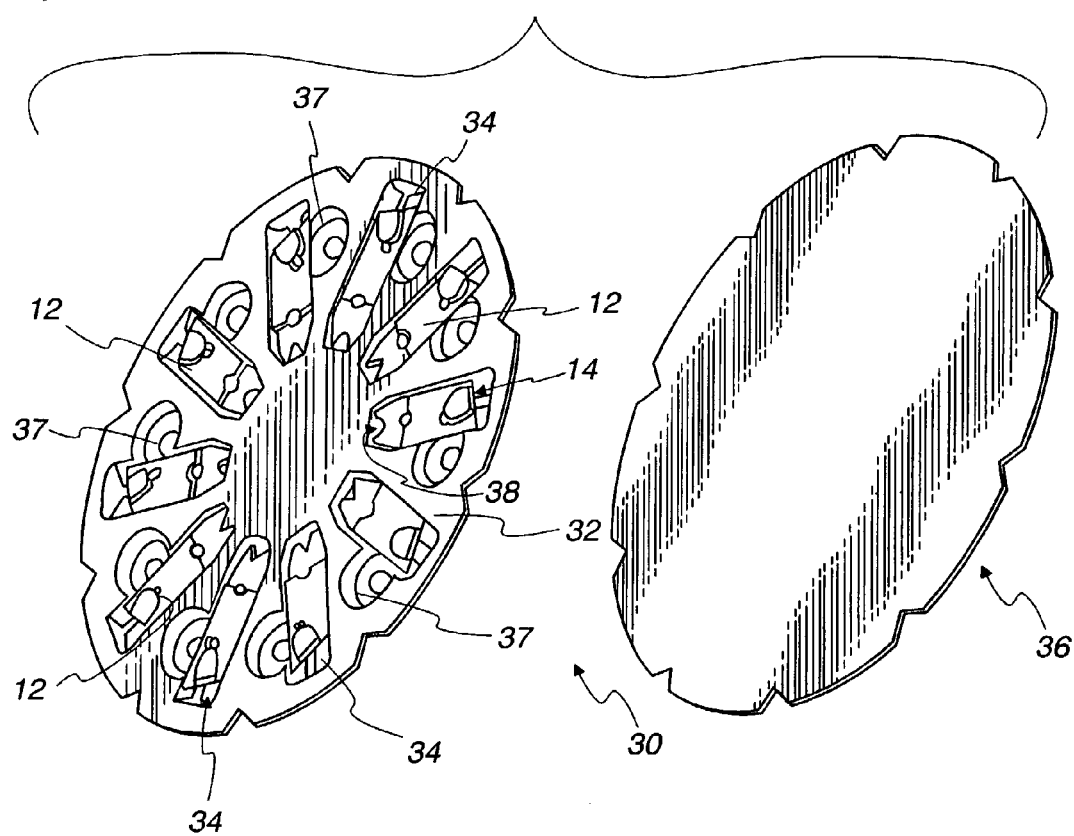
FIG. 2 is a perspective view of a prior art sensor pack having a foil lid removed.

As discussed in the background section, the testing device 130 and sensor pack 100 are advantageous because the sensor pack 100, or the number of sensor packs 100, are independent of and are not constrained by the size of the testing device. For example, referring to the prior art shown in FIGS. 1 and 2, the size of the sensor pack 30 is constrained by the size of the testing device 10, because the sensor pack 10 is housed within the testing device 10. Accordingly, it would appear to be difficult to modify the design of the sensor pack 30 to have more than the ten test sensors 12 disposed within the sensor pack 30.

Figure 8:
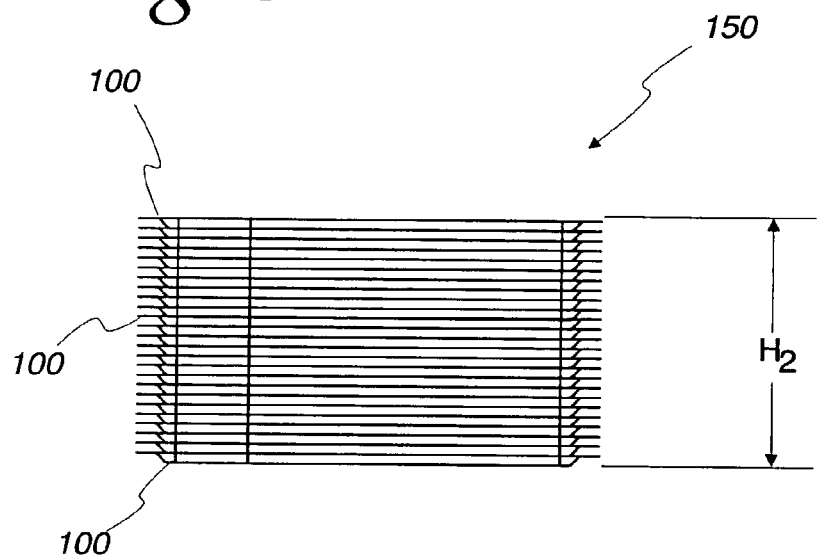
FIG. 8 is a side view of a stack of test sensors according to the present invention.

Referring now to FIG. 8, a sensor pack stack 150 is shown. The sensor pack stack 150 is made up of a plurality of sensor packs 100 stacked one top of one another. While the sensor pack stack 150 illustrated in FIG. 8 comprises twenty-five test sensors 100, other sensor pack stacks can include any number of test sensors 100 because a sensor pack stack (of any size) will not be housed within the testing device 130. The sensor stack pack 150 comprising twenty-five test sensors 120 has a height $H_2$ of approximately one inch (about 25.4 mm). The inventor envisions that, in accordance with the present invention, the sensor packs 100 will be commercially available in sensor stack pack stacks of a variety of sizes. In an alternative embodiment, loose sensor packs 100 are commercially available in a container such as a box or bag.

Figure 9:
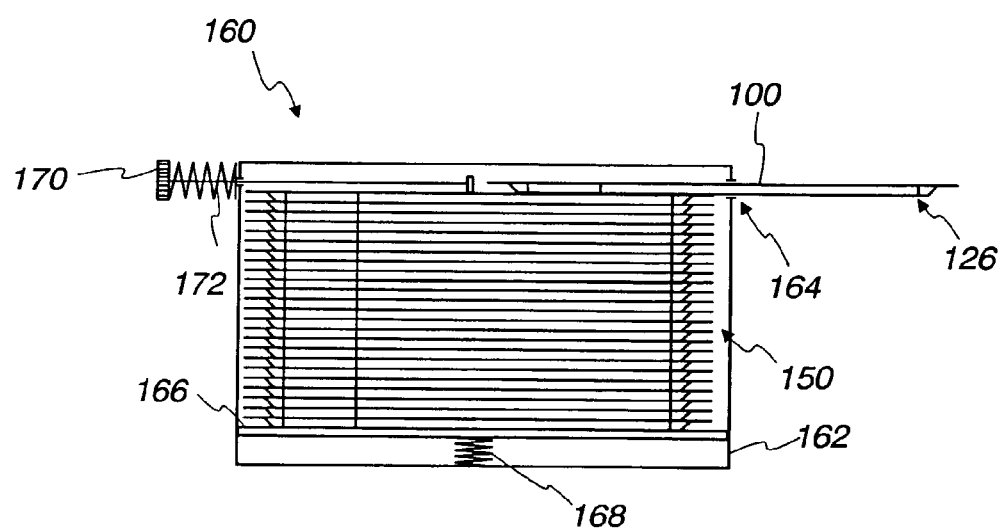
FIG. 9 is a side view of a sensor pack dispensing mechanism according to the present invention.

Referring now to FIG. 9, a sensor pack dispenser 160 is shown. The dispenser 160 is adapted to house a sensor pack stack 150 and to dispense individual sensor packs 100. The dispenser 160 includes a housing 162 and an outlet 164 in the housing 162 through which the individual sensor packs 100 are dispensed. The sensor packs 100 are dispensed such that the contact end 126 of the test sensor 120 disposed with the sensor pack 100 is extended through the outlet 164 According to one embodiment, the end of the sensor pack corresponding to the contact end 126 is pushed directly into the testing device. Within the dispenser 160, the stack 150 rests on a platform 166 which is pressed upward by a spring 168. In order to dispense an individual sensor pack 100, a plunger 170 is depressed, which forces the uppermost sensor pack 100 through the outlet 164 as shown in FIG. 9. A spring 172 moves the plunger 170 to its home position (not show, to the left as viewed in FIG. 9) to make way for the spring 168 to move the platform 166, and in turn the stack 150, upward. At this point, depressing the plunger 170 would dispense a new sensor pack 100.

Referring now to FIG. 10, a card 180 having a plurality of sensor/desiccant cavities 182 is shown. While a sensor pack card 180 may contain any number of test sensors 120, the card 180 illustrated in FIG. 10 holds twenty test sensors and has a length $L_3$ of approximately 3.64 inches (about 92.46 mm) and a width $W_3$ of approximately 2.25 inches (about 57.15 mm). According to one embodiment, the card 180 is made of a single base 184 having a plurality of sensor/desiccant cavities 182 disposed therein and a single foil cover. In such an embodiment, the foil cover is heat sealed to the outer peripheral edges of the base and about the perimeter of each set of the sensor/desiccant cavities disposed in the base to isolate each of the sensor/desiccant cavities from each other. Each of the test sensors 120 are disposed in the card 180 such that the contact end 126 is disposed adjacent the outer periphery of the card 180. This arrangement allows the card 180 to be pushed into the testing device (FIGS. 6 and 7) to extract a test sensor 120 from the card.

While the present invention has been described and illustrated in connection with electrical biosensors, the present invention is applicable to other types of test sensors including optical biosensors. As discussed in the background section, optical biosensors are described in U.S. Pat. No. 5,194,393, which is incorporated herein by reference above. Additionally, the present invention is applicable to other configurations of biosensors, such as biosensors that do not have a contact area and a collection area disposed at opposite ends of the test sensor, but have the collection area disposed on other areas of the test sensors including on the side or on the top of the test sensor. Regardless of the type of sensor employed in the analysis, the present invention provides the described advantages to the overall testing process.

While the invention is susceptible to various modifications and alternative forms, specific embodiments thereof have been shown by way of example in the drawings and herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

What is claimed is:

1. A method for loading a test sensor disposed within a sensor package into a testing device, the method comprising the acts of:

providing the sensor package including a protective covering and the test sensor, a first end of the test sensor having at least one pointed portion;

inserting a portion of the sensor package into an inlet region of the testing device such that the sensor package engages the testing device to load the test sensor but remains at least generally external to the testing device, the inlet region including a guide member that is adapted to assist in the proper alignment of the inserted portion of the sensor package within the testing device, the sensor package being inserted such that (i) a first end portion of the protective covering and the first end portion of the test sensor resides in the inlet region of the testing device and (ii) a second end portion of the protective covering and a second end portion of the test sensor remains outside of the testing device;

lowering a package-puncturing member of the testing device into the inlet region, the package-puncturing member adapted to puncture the inserted portion of the sensor package;

puncturing the inserted portion of the sensor package with the package-puncturing member;

removing the protective covering by pulling a section of the sensor package in a direction away from the testing device, the at least one pointed portion of the test sensor assisting in removal of the sensor package such that the at least one pointed portion punctures the protective covering thereby allowing the removal of the protective covering; and maintaining the first end portion of the test sensor in the inlet region of the testing device in a testing position.

2. The method of claim 1 wherein the test sensor is an electrical biosensor, the first end portion of the electrical biosensor being a contact end and the second end portion of the electrical biosensor being a collection end, the contact end of the electrical biosensor disposed toward an outer periphery of the sensor package, and wherein inserting further comprises inserting the portion of the sensor package corresponding to the outer periphery of the sensor package, the inserted portion corresponding to the contact end of the electrical biosensor.

3. The method of claim 1 wherein the first end portion of the test sensor includes a contact area located on a first side of the test sensor and the second end portion of the test sensor includes a collection area located along another side of the test sensor, the test sensor being disposed within the sensor package such that the contact area is disposed adjacent an outer periphery of the sensor package.

4. The method of claim 1 wherein the test sensor is an electrical biosensor having a contact area and a collection area.

5. The method of claim 1 wherein the act of removing further comprises electrically coupling a pair of terminals disposed in the inlet region of the testing device to a pair of terminals disposed on the test sensor.

6. The method of claim 1 wherein the protective covering further comprises a base having a cavity adapted to contain the test sensor and a foil cover adapted to cover the base.

7. The method of claim 6 wherein the foil cover is sealed to an outer periphery of the cavity.

8. The method of claim 7 wherein the cavity has a substantially rectangular shape, the cavity having two side walls, two end walls, a bottom, and an outer periphery, at least one of the two end walls upwardly sloping from the bottom towards the outer periphery.

9. The method of claim 6 wherein the cavity includes a test sensor cavity adapted to contain the test sensor and a desiccant cavity adapted to contain a desiccant.

10. The method of claim 1 wherein the sensor package includes a desiccant.

11. The method of claim 1 wherein the protective covering includes a base having a plurality of cavities, each of the plurality of cavities being adapted to contain one test sensor.

12. The method of claim 11 wherein the protective covering further comprises a foil cover sealed to the base along an outer periphery of each of the plurality of cavities.

13. The method of claim 1 wherein the test sensor is an optical biosensor.

14. A testing device for, analyzing the glucose concentration of a sample of blood adapted to remove a test sensor from a sensor package, the sensor package containing at least one test sensor and a protective covering, the testing device comprising:

an inlet region for receiving a portion of the sensor package such that the sensor package engages the testing device to load the test sensor but remains at least generally external to the testing device, a first end of the test sensor having at least one pointed portion, the inlet region including a guide member adapted to assist in the proper alignment of the received portion of the sensor package within the testing device, the sensor package having an outer periphery, the received portion of the sensor package corresponding to a first end portion of the protective covering and the first end portion of the test sensor and the unreceived portion of the sensor package corresponding to a second end portion of the protective covering and a second end portion of the test sensor; and a package-puncturing member adapted to extend into the inlet region, puncture the sensor package, and engage a mating feature of the test sensor disposed towards the first end portion of the test sensor to hold the test sensor in the inlet region during testing of the fluid sample and a pair of terminals disposed in the inlet region adapted for electrically coupling a pair of terminals disposed on the test sensor to the testing device, wherein the at least one pointed portion of the test sensor assists in removal of the sensor package such that the at least one pointed portion punctures the protective covering thereby allowing the removal of the protective covering.

15. The testing device of claim 14 wherein the test sensor is an electrical biosensor.

16. The testing device of claim 15 wherein the first end portion of the test sensor is a contact end and the second end portion of the test sensor is a collection end, the test sensor disposed within the sensor package such that the contact end is disposed adjacent the outer periphery of the sensor package.

17. The testing device of claim 15 wherein the first end portion of the test sensor includes a contact area located on a first side of the test sensor and the second end portion of the test sensor includes a collection area located along another side of the test sensor, the test sensor being disposed within the sensor package such that the first end portion is disposed adjacent the outer periphery of the sensor package.

18. The testing device of claim 15 wherein the electrical biosensor includes a contact area and a collection area.

19. The testing device of claim 14 wherein the protective covering comprises a base having a cavity for containing the test sensor and a foil cover for covering the base.

20. The testing device of claim 19 wherein the foil cover is sealed to an outer periphery of the cavity.

21. The testing device of claim 19 wherein the cavity has a substantially rectangular shape, the cavity having two side walls, two end walls, a substantially flat bottom, and an outer periphery, at least one of the two end walls upwardly sloping from the bottom towards the outer periphery.

22. The testing device of claim 21 wherein the test sensor is disposed in the cavity such that the first end portion of the test sensor is disposed adjacent the at least one sloped end wall, the first end portion of the test sensor corresponding to a contact end.

23. The testing device of claim 19 wherein the cavity includes a test sensor cavity for containing the test sensor and a desiccant cavity for containing a desiccant.

24. The testing device of claim 14 wherein the sensor package includes a dessicant.

25. The testing device of claim 14 wherein the protective covering includes a base having a plurality of cavities, each of the plurality of cavities being adapted to contain one test sensor.

26. The testing device of claim 25 wherein the protective covering includes a foil cover sealed to the base along an outer periphery of each of the plurality of cavities.

27. The testing device of claim 14 wherein the test sensor is an optical biosensor.

28. The method of claim 1, wherein the act of providing the sensor package further includes providing the sensor package with a stack of sensor packages, the stack including a plurality of sensor packages stacked on top of one another such that the top sensor package is dispensed and inserted into the inlet region of the testing device.

29. The method of claim 1, wherein the act of providing the sensor package includes providing the sensor package from a card of sensor packages, the card including a plurality of sensor packages arranged to form a row of sensor packages, and wherein a portion of the card having a sensor package is inserted into the inlet region of the testing device.

30. The testing device of claim 14, wherein the sensor package is provided from a stack of sensor packages, the stack including a plurality of sensor packages stacked on top of one another such that the top sensor package is dispensed and inserted into the inlet region of the testing device.

31. The testing device of claim 14, wherein the sensor package is provided from a card of sensor packages, the card including a plurality of sensor packages arranged to form a row of sensor packages, and wherein a portion of the card having a sensor package is inserted into the inlet region of the testing device.

32. The method, of claim 1, wherein the testing device is adapted to determine the concentration of blood glucose.

33. A testing device adapted to remove a test sensor from a sensor package, the sensor package containing at least one test sensor and a protective covering, the testing device comprising:

an inlet region for receiving a portion of the sensor package such that the sensor package engages the testing device to load the test sensor but remains at least generally external to the testing device, a first end of the test sensor having at least one pointed portion, the inlet region including a guide member adapted to assist in the proper alignment of the received portion of the sensor package within the testing device, the sensor package having an outer periphery, the received portion of the sensor package corresponding to a first end portion of the protective covering and the first end portion of the test sensor and the unreceived portion of the sensor package corresponding to a second end portion of the protective covering and a second end portion of the test sensor; and a package-puncturing member adapted to extend into the inlet region, puncture the sensor package, and engage a mating feature of the test sensor disposed towards the first end portion of the test sensor, to hold the test sensor in the inlet region during testing of a fluid sample and a pair of terminals disposed in the inlet region adapted for electrically coupling a pair of terminals disposed on the test sensor to the testing device, wherein the at least one pointed portion of the test sensor assists in removal of the sensor package such that the at least one pointed portion punctures the protective covering thereby allowing the removal of the protective covering.

* * * * *